United States Patent [19]
Honda et al.

[11] Patent Number: 6,100,922
[45] Date of Patent: Aug. 8, 2000

[54] APPARATUS FOR RECOGNIZING AN ELECTRONIC COMPONENT

[75] Inventors: Hiroshi Honda; Yutaka Ogura; Hiroshi Anzai, all of Chofu, Japan

[73] Assignee: Juki Corporation, Tokyo, Japan

[21] Appl. No.: 09/163,077

[22] Filed: Sep. 29, 1998

Related U.S. Application Data

[63] Continuation-in-part of application No. 09/103,362, Jun. 23, 1998.

[51] Int. Cl.$^7$ ...................................................... H04N 7/18
[52] U.S. Cl. .......................... 348/86; 356/138; 356/375; 356/399; 358/101; 414/737; 414/752
[58] Field of Search ............................... 348/86; 356/375; 29/740, 741, 721, 759

[56] References Cited

U.S. PATENT DOCUMENTS

| | | | |
|---|---|---|---|
| 4,793,707 | 12/1988 | Hata et al. ................................. | 356/375 |
| 5,131,139 | 7/1992 | Oyama et al. . | |
| 5,519,495 | 5/1996 | Kawaguchi ............................... | 356/375 |
| 5,724,722 | 3/1998 | Hashimoto ................................ | 29/740 |

FOREIGN PATENT DOCUMENTS

| | | |
|---|---|---|
| 4-46000 | 7/1992 | Japan . |
| 2520596 | 12/1996 | Japan . |

*Primary Examiner*—Chris S. Kelley
*Assistant Examiner*—Shawn S. An
*Attorney, Agent, or Firm*—Milbank, Tweed, Hadley & McCloy LLP

[57] ABSTRACT

An improved apparatus for photographing and recognizing an absorbed component is provided comprising a vacuum nozzle which includes a main body portion having a larger outer size than that of the absorbed component and a tapered surface formed at the lower portion of the nozzle as a light diffusing surface. A plurality of first light sources are situated above the absorbed component at multiple heights are provided for back lighting the absorbed component. The tapered surface is formed in such a manner that the absorbed component is lighted by back lighting from the plurality of first light sources reflected off the tapered surface and selectively turned on according to the up/down movement of the vacuum nozzle, according to the type of the component.

5 Claims, 9 Drawing Sheets

(SSOP, QSOP)

(C)

(QFP, TQFP)

(D)

(QFP)

(E)

(MELF)

(F)

(PLCC)

(G)

(SOJ)

(H)

(BGA)

APPARATUS FOR RECOGNIZING AN ELECTRONIC COMPONENT

CROSS REFERENCE TO RELATED APPLICATIONS

This application is a continuation in part of application Ser. No. 09/103,362, filed Jun. 23, 1998.

BACKGROUND OF THE INVENTION

The present invention relates to an apparatus for recognizing electronic components and more particularly to an apparatus for photographing and recognizing an electronic component by back lighting or front lighting without changing the vacuum nozzle according to the kind of component.

In Japanese Patent Publication No. Hei 8-24234 (U.S. Pat. No. 5,131,139), a component mounting machine is described which has a nozzle with a larger outer size than that of a component absorbed to the nozzle. A tapered surface is formed on the lower portion of the nozzle as a light diffusing surface and the size of the lower end of the nozzle is smaller than that of the component. A light source is placed under the nozzle which radiates light upwardly towards a diffuser means disposed above the nozzle. The light is then diffused downward to a tapered surface on the nozzle, which becomes bright. The absorbed component is clearly observed as a black silhouette inside the bright tapered surface by a camera disposed below the moving path of the nozzle.

The Japanese Utility Model Registration No. 2520596 (Laid-Open Publication No. Hei 4-631771) describes a vacuum nozzle which has a tapered, mirror-finished surface. The reflected light from the absorbed component is observed by a camera disposed opposite to the component. This arrangement prevents the reflected light from the tapered surface from being observed by the camera as incident light.

Japanese Patent Publication No. Hei 4-46000 describes an apparatus for detecting the position of a component which includes two light sources. One is placed above the absorbed component and the other is placed below the absorbed component. The light from the upper light source is radiated at the component through a diffusion plate and the component is photographed by a camera disposed under the component (which arrangement is called "back lighting"). The light from the lower light source is radiated at the component through another diffusion plate with an aperture therein. The reflected light from the component is then photographed through the aperture by the camera (which arrangement is called "front lighting").

Several problems arise, however, in using the structure described in U.S. Pat. No. 5,131,139. Many types of components are used in a component mounting machine, such as rectangular chips, SOP (Small Outline Package), QFP (Quad Flat Package), MELF (Metal Electrode Face), PLCC (Plastic Leaded Chip Carrier), SOJ (Small Outline J-leaded package), BGA (Ball Grid Array package), etc. Among these components, such components as rectangular chips, SOP, QFP, MELF, etc. can be recognized precisely, but PLCC, SOJ, BGA, etc., which have their leads on the back side of the components, are difficult to recognize accurately since only back lighting is usable with this structure. Therefore, other means of capturing the reflected image of these components, (front lighting, for example) is required in order to capture the image precisely. Another disadvantage of this structure is that the light source disposed below the component is mounted in a ring arrangement, which needs a wider area. Furthermore, in order to confine the light source to a small area by using a smaller diameter ring light with narrow directivity, additional elements like lenses would be needed, which leads to a high cost for the apparatus.

With the structure described in Japanese Utility Model Registration No. 2520596, components such as rectangular chips, SOP, QFP, etc. can be recognized but with less accuracy than by recognizing them by the aforementioned back lighting arrangement. PLCC, SOJ, BGA, etc. components are possible to recognize, but cylindrical components like MELF are difficult to recognize with high accuracy because only front lighting can be used. Moreover, a diffusion plate must be placed over the nozzle so that only the reflected light from the component is incident on the camera, eliminating other reflected light, or the area of the mirrored tapered surface of the nozzle must be wider than that of the recognizing means, which leads to a higher cost apparatus.

In both of the aforementioned structures, the size of the lower end of the nozzle must be smaller than that of the component. Therefore, the mechanical strength of the nozzle is weakened when a tiny size component is to be absorbed.

Still further problems arise when the structure described in the Japanese Patent Publication No. Hei 4-46000 is adopted, although this structure has both back lighting means and front lighting means. Both of the light sources have to be diffused by diffusion plates when lighting the absorbed component. While there is enough space under the nozzle, it is difficult to find enough space to mount the light source and the diffusion plate above the nozzle, and so this structure requires a complicated arrangement.

It is therefore an object of the present invention to provide an apparatus for recognizing precisely the component absorbed by the vacuum nozzle by using back lighting or front lighting without additional diffusion plates.

In order to solve the problems mentioned above, the present invention employs an apparatus for photographing and recognizing an absorbed component comprising a vacuum nozzle which includes a main body portion having a larger outer size than that of the absorbed component and a tapered surface formed at the lower portion of the nozzle as a light diffusing surface, a first light source and a second light source for lighting the absorbed component. The tapered surface is formed in such a manner that the absorbed component is lighted by back lighting from the first light source reflected off the tapered surface or is lighted by front lighting from the second light source, according to the type of the component.

With the arrangement described above, the direction of the diffused light on the tapered surface is changed according to the selection of one of the two light sources, since the tapered surface is formed at a predetermined angle with the nozzle axis. Thus, precise recognition can be attained by employing back lighting or front lighting of the component as appropriate.

This tapered surface can be made by sandblasting after machining (for example, by lathing) in order to get the desired reflecting/diffusing characteristics.

When recognizing the absorbed component, only the image taken adjacent to the detected contour of the tapered surface, which includes the image of the absorbed component, is processed. Therefore, image processing time and the area of the tapered surface can be reduced.

If the suction surface at the lower end of the nozzle is made of light absorbing material (deluster coated material or ceramic), the size of the suction surface can be larger than that of the absorbed component. Therefore, the mechanical strength of the nozzle can be increased in case a tiny size component is to be absorbed.

In still another embodiment, a plurality of light sources for back lighting are mounted on four walls separated by different sized spaces from each other. The light sources surround the vacuum nozzle for lighting the tapered surface with even brightness. This arrangement lights the absorbed component evenly by back lighting reflected off the tapered surface. This method can improve the accuracy of recognizing the component.

The first light sources for back lighting as described above are disposed at multiple heights in the direction of the up/down movement of the vacuum nozzle. Predetermined light sources facing the tapered surface are selectively turned on according to the up/down movement of the vacuum nozzle in response to the thickness of the absorbed component. This means of back lighting can avoid excessive light intensity on unnecessary portions of the tapered surface 5, prevent bad effects in recognition of the component, and results in a reduction of power consumption.

DETAILED DESCRIPTION OF THE DRAWINGS

Embodiments of the present invention will be explained in detail with reference to the attached drawings.

Figure 1:
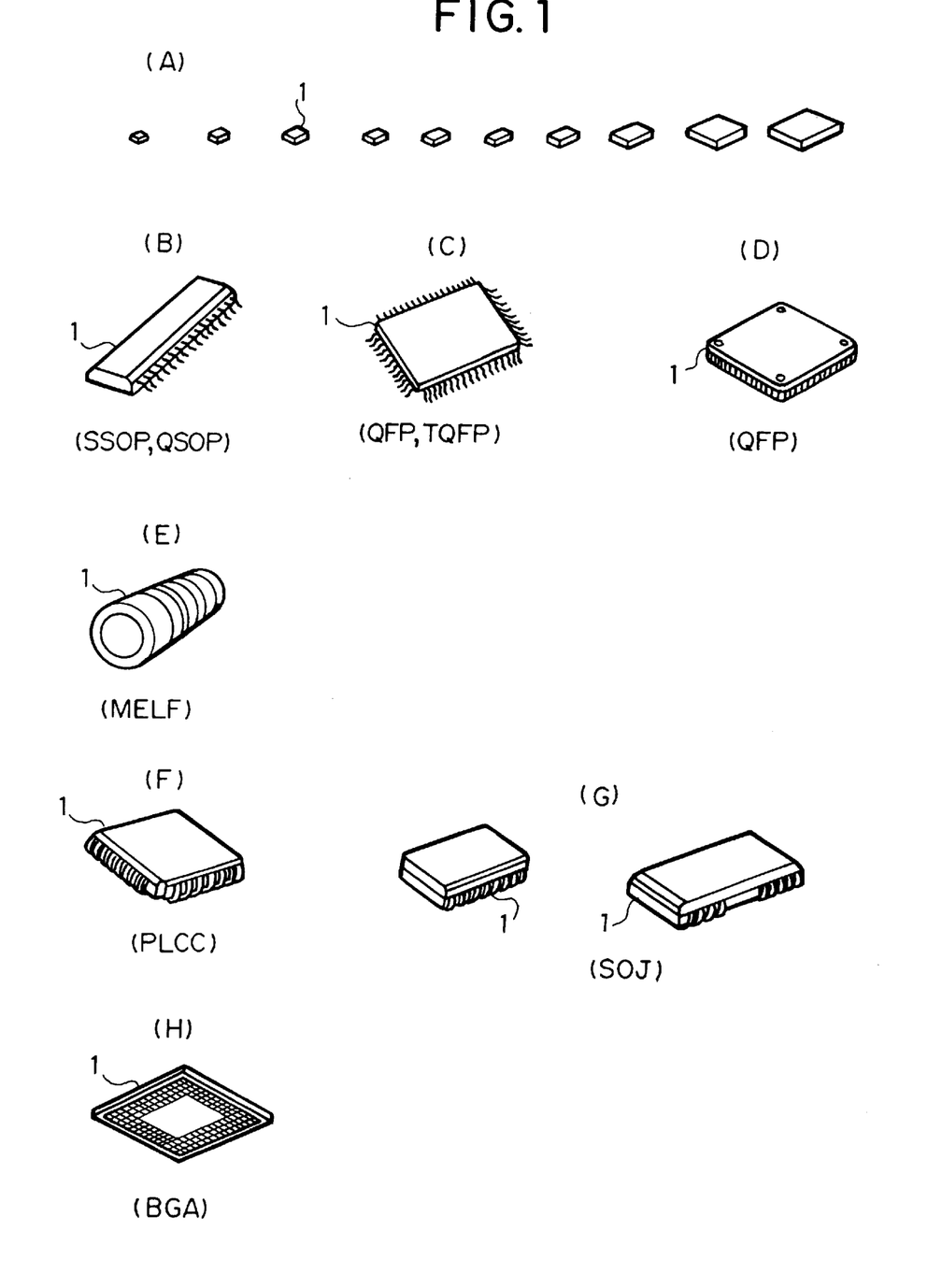
FIG. 1 is a series of perspective diagrams (A) to (H) of various kinds of electronic components.
Figure 2:
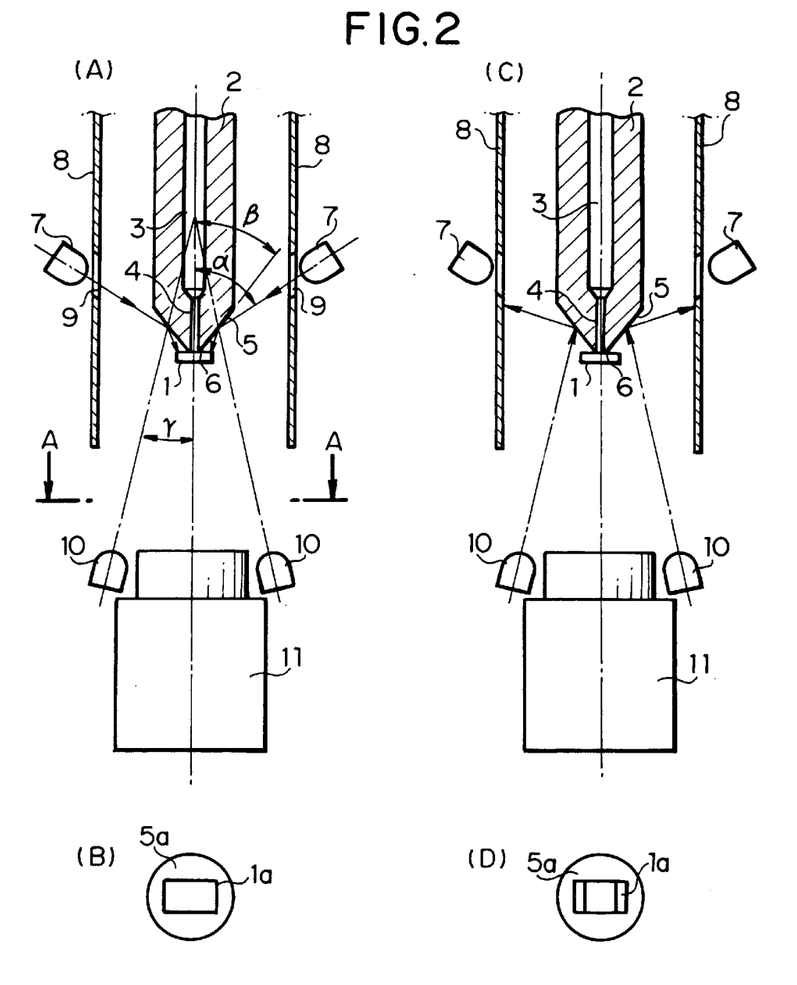
FIG. 2 is a series of diagrams (A) to (D) illustrating the recognition of components by back lighting (A) or front lighting (C), and their images (B) or (D) respectively.
Figure 7:
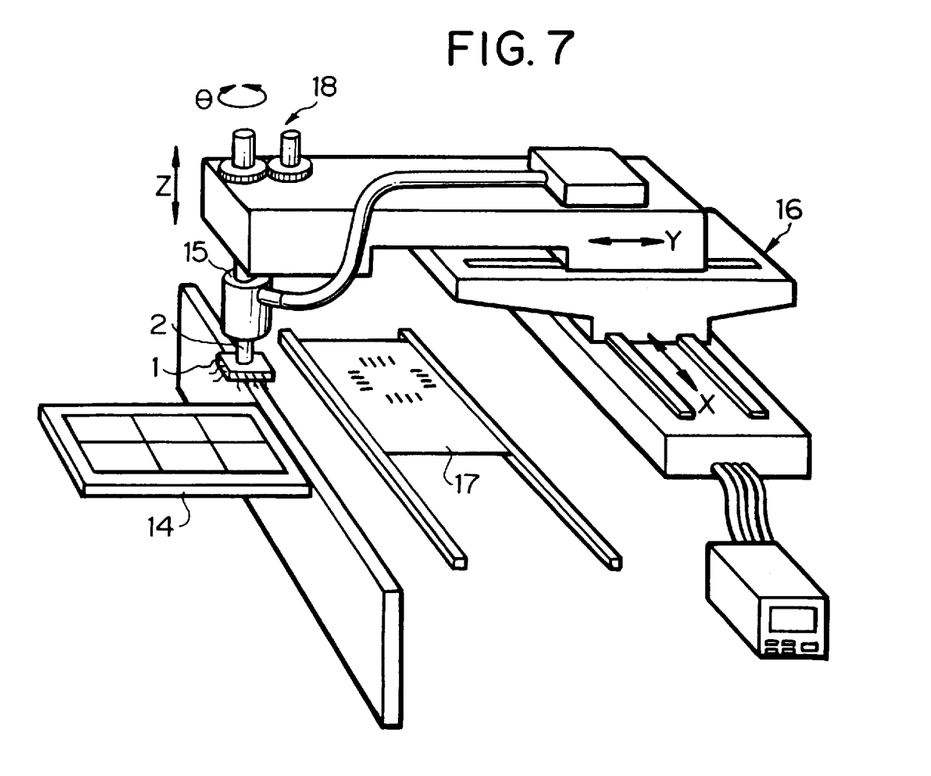
FIG. 7 is at perspective view showing a portion of the component mounting machine.

A component storage section 14 in the component mounting machine shown in FIG. 7 contains many components, such as rectangular chips, SOP, QFP, MELF, etc. shown in FIG. 1(A) to (H). A head unit 15 having one or more vacuum nozzles 2 as also shown in FIG. 2 is moved to the component storage section 14 driven by XY mechanism 16, and the vacuum nozzle is lowered by up/down driving mechanism (not shown). Negative pressure is generated through a vacuum conduit 3 and a passage 4 to pick up component 1 by the nozzle 2. The head unit 15 is then transported to a printed circuit board 17 moving in XY directions and the component is placed in a predetermined position on the circuit board 17.

While the bead is moving from the storage section 14 to the circuit board 17, the orientation of the absorbed component 1 is recognized in its absorbed condition by a recognizing camera 11 (composed of a CCD, for example). Deviations in the angular and coordinate orientation of the component are compensated for, and the component is placed on the board 17 with accuracy.

Referring to FIG. 2, a cylindrical light absorption plate 8 is placed with an aperture 9 bored therein and a first light source 7 (composed of LEDs, for example) is positioned facing this aperture. The light source 7 is located above the suction surface 6 of the nozzle 2 and tapered surface 5 is formed adjacent the suction surface 6. When the light 7 is turned on, the light passes through the aperture 9, is radiated to the tapered surface at a certain angle, and reflected therefrom toward the absorbed component 1 from above. In this case, the optical axis of the light source 7 is set to an angle $\alpha$ with the nozzle center axis, and the angle of the tapered surface 5 with the nozzle center axis is set to $\beta$.

The tapered surface 5 is machined (for example, by lathing), without requiring a grind process, and is finished by sandblasting, for example, to impart diffusing characteristics. The diameter of the nozzle 2 is made larger than the anticipated maximum size of the components so that it is not necessary to change the nozzle when the type or size of the component is changed. When the lower end of the nozzle 2 (suction surface 6) is made of light absorbing material (deluster coated material or ceramic), the size of the surface 6 can be larger than that of the absorbed component 1. Therefore, the mechanical strength of the nozzle can be increased in case a tiny size component is to be absorbed.

The second light source 10 (composed of LEDs, for example) and the recognizing camera 11 with lens are located underneath, opposite the suction surface 6 of the nozzle 2. The optical axis of the second light source is set to an angle $\gamma$ with the nozzle center axis. When the second light source is turned on, the absorbed component 1 is lighted from underneath. The incident light radiating to the tapered surface 5 from the second light source is diffused to the side of the nozzle, a part of which light is absorbed into the light absorption plate 8.

Figure 3:
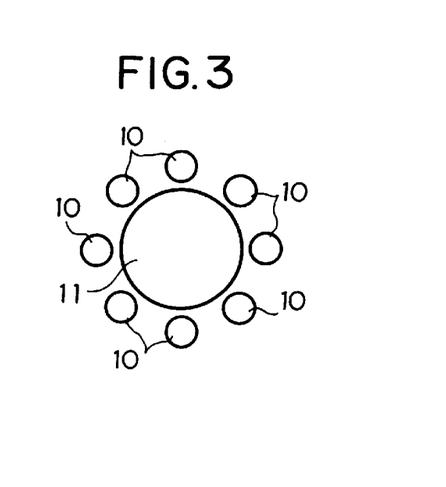
FIG. 3 is a diagram illustrating the disposition of light sources around a recognizing camera.

A plurality of the second light sources 10 (for example 8 pieces) are disposed around the recognizing camera 11 at an equal distance from each other. Similarly, a plurality of the first light sources 7 are disposed around the light absorption plate 8 facing apertures 9. The relation among the aforementioned angles $\alpha$, $\beta$, $\gamma$, is set to:

$(\pi/2+\beta)>\alpha$ and $(\pi/2-\beta)>\gamma$.

The process in the component mounting machine when using components such as a rectangular chip, SOP, QFP, MELF, etc. is as follows: the head unit 15 having an absorbed component 1 is first transported into the field of view of the recognizing camera 11. The first light source 7 is turned on, the light passes through aperture 9 in the light absorption plate 8, it is reflected by the tapered surface 5, and the component 1 is lighted from the upper side. Since the light is also diffused on the tapered surface 5, the component 1 is photographed by the recognizing camera 11 as a black shadow 1a with the bright background 5a of the tapered surface 5 as shown in FIG. 2(B). The component 1 can be recognized clearly without depending on its surface characteristics.

When mounting components such as rectangular chips, PLCC, SOJ, BGA, etc., the second light source 10 is turned on, the light from the source 10 is reflected from the component 1 as shown in FIG. 2(C) and the reflected image is photographed by the camera 11. At this time, the light around the component 1 is reflected by the tapered surface partially towards the light absorption plate 8 by the tapered surface and so absorbed, and partially onto the component. However, since the reflected light from the component is brighter than diffused light, the image 1a of a component like a rectangular chip is photographed by the camera 11 with good contrast to the image 5a of the tapered surface as shown in FIG. 2(D). Therefore, a component having leads or terminals on the baLckside of it can be recognized precisely.

In the embodiment described above, either of the first or the second light source is turned on. As another modification, such an arrangement can be made where both of the first and second light source are always powered on and optical shutter devices are disposed in front of each light source. Back lighting or front lighting can be attained by opening or closing these shutters. It is also possible to have both of the light sources always powered on with one of the light sources set dimmer as compared with the other one.

Figure 4:
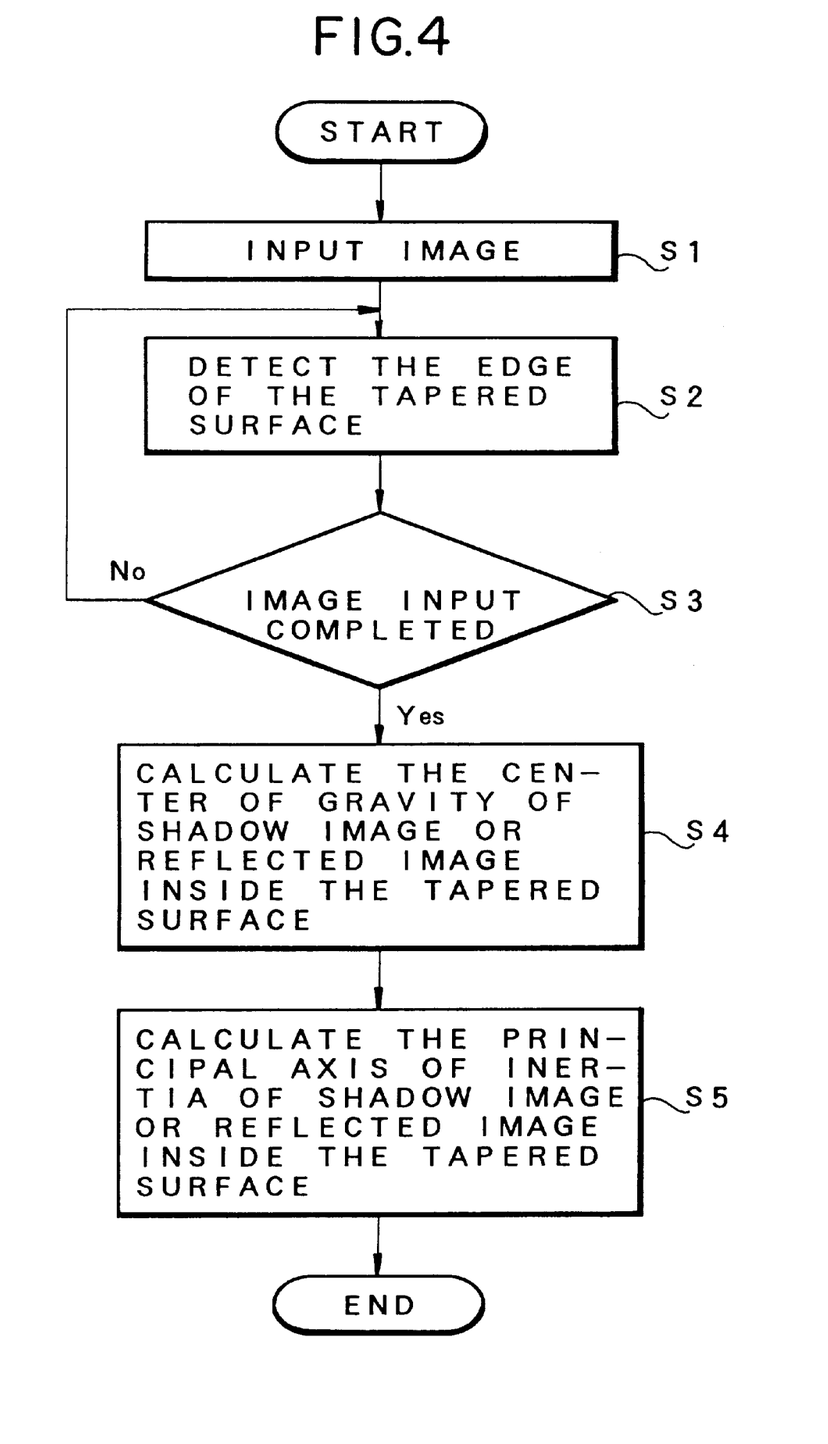
FIG. 4 is a flow chart showing the process of recognizing a component.

FIG. 4 describes a flow chart for the process of recognizing the absorbed component 1. The recognizing camera 11 photographs the absorbed component 1, detects the edge of the tapered surface of the nozzle, calculates its center and processes the adjacent image including the image of the component 1.

At step 1 in FIG. 4 the image from the camera 11 is input. The position of the edge of the image, 5a of the tapered surface (as in FIG. 2(B) and (D)) is detected at step 2. If the image input is completed at step 3, the center of gravity of the shadow image 1a or the reflected image 1a (in the case of back lighting as shown in FIG. 2(A) or front lighting as shown in FIG. 2(C), respectively) inside the image 5a detected at step 2 is calculated at step 4. At step 5 a principal axis of inertia of the shadow image or reflected image 1a inside the image 5a of the tapered surface is calculated as well as the angular orientation.

Thus, the deviation of the actual position of the absorbed component from the predetermined position is calculated. The deviation $\Delta\theta$ of the angular orientation is compensated for by rotation about the nozzle axis driven by rotating mechanism 18 in FIG. 7 and the deviation $\Delta X$, $\alpha Y$ from lateral (X,Y) position is compensated for by XY driving mechanism 16. Then the absorbed component 1 can be placed onto the circuit board 17 accurately.

Figure 5:
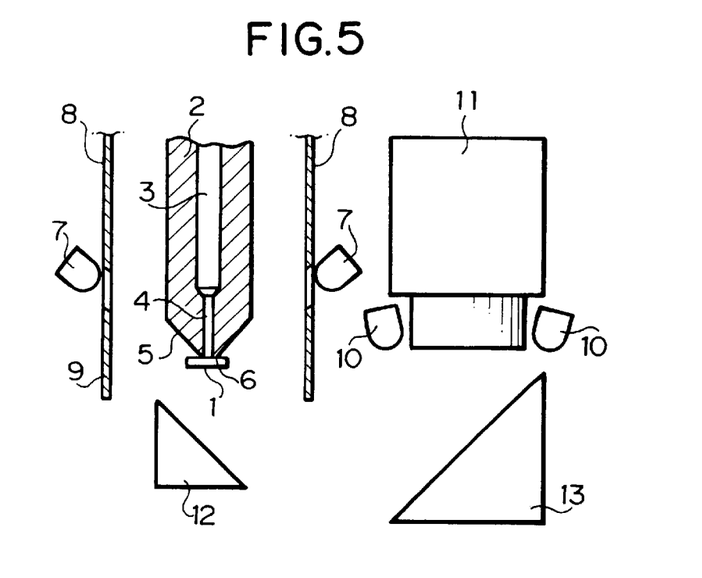
FIG. 5 is a schematic view showing another embodiment of the present invention.
Figure 6:
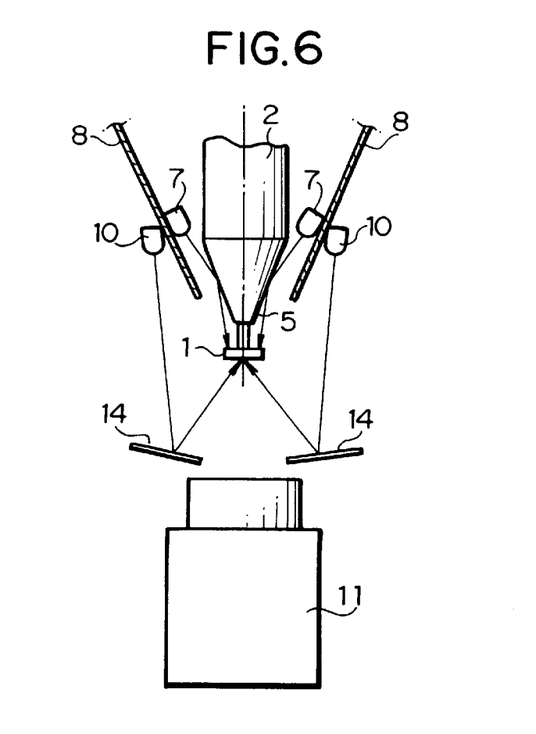
FIG. 6 is a schematic view showing still another embodiment of the present invention.

Other embodiments of the present invention are shown in FIG. 5 and FIG. 6. In each drawing, the same reference numerals are given to the same elements shown in FIG. 2.

In the embodiment shown in FIG. 5, the recognizing camera 11 is disposed on the same head unit as vacuum nozzle 2. The recognizing camera 11 and the second light source 10 are not disposed under the suction surface, but to the side of the vacuum nozzle. A movable prism (or mirror) 12 and a fixed prism (or mirror) 13 are placed in order to light the component from underneath. At the time the component is photographed, the movable prism moves into the light path for front lighting the component, the light from the light source 10 being reflected by the fixed prism and the movable prism. The incident light radiated toward the tapered surface 5 is reflected and diffused to the side in the same manner as the embodiment shown in FIG. 2.

In the embodiment described above, the characteristics of the absorbed component can be recognized while the head unit is transported from the pick-up position to the placement position. The movable prism 12 is moved out of the up/down path of the nozzle when a component is picked up or placed.

In the embodiment as shown in FIG. 6, the tapered surface 5 is formed at a smaller angle with the nozzle axis than in previous embodiments. The second light source 10 can be disposed above the nozzle, the same as the first light source 7. The tapered surface 5 optically functions in the same manner as shown in FIG. 2 or FIG. 5.

Still another embodiment will be explained hereinafter. The first light sources for back lighting the component are disposed at multiple heights in the direction of the up/down movement of the vacuum nozzle 2. Predetermined light sources are selectively turned on according to the up/down movement of the vacuum nozzle in response to the thickness of the absorbed component.

Figure 8:
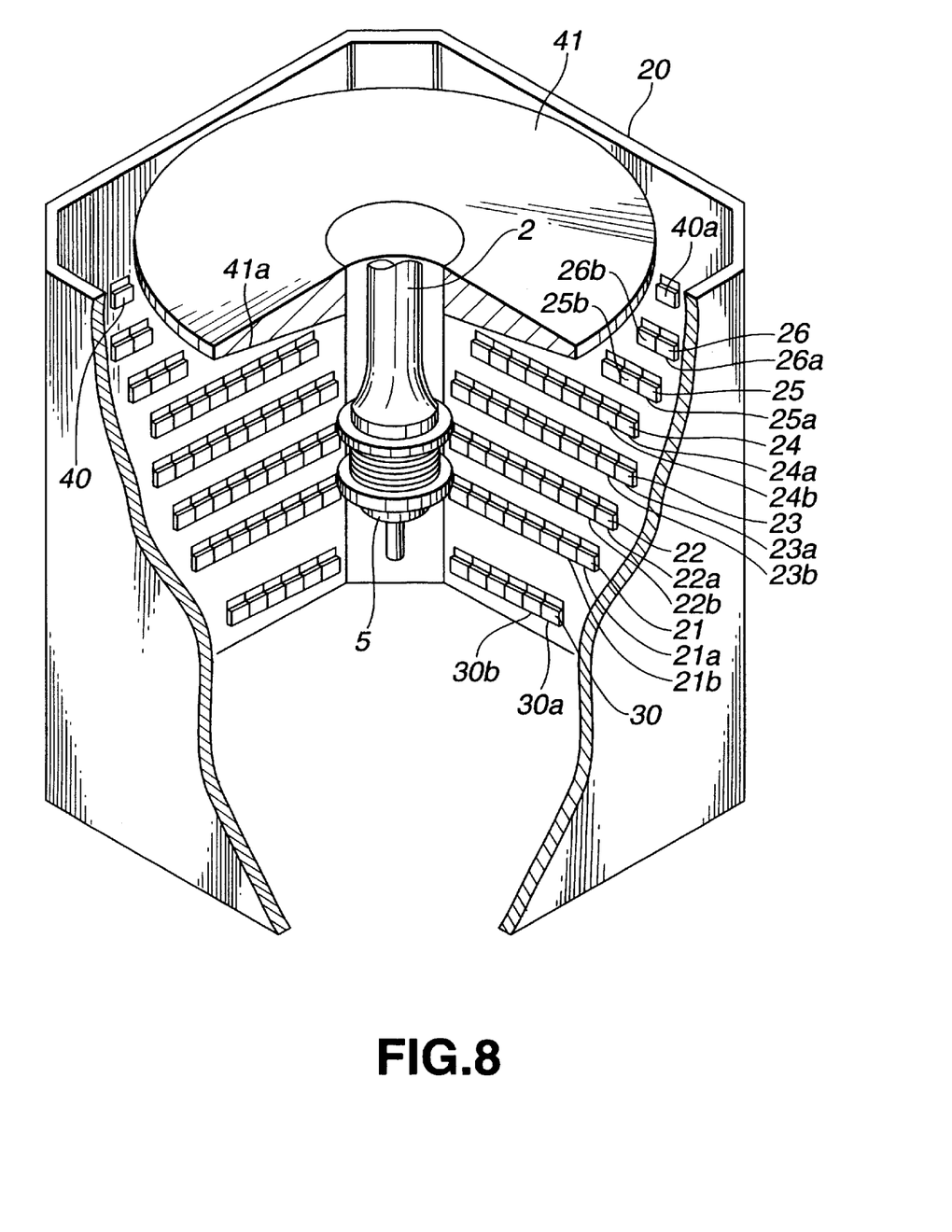
FIG. 8 is a cutaway perspective diagram illustrating a mounting structure for the light sources for back lighting at multiple heights.

As shown in FIG. 8, light sources 21 to 26 (which correspond to the first light source 7) for back lighting an absorbed component like a QFP are mounted at multiple heights on the side walls of a rectangular illumination unit with cylindrical comers 20. The light source 21 for back lighting is composed of a plurality of LED light sources 21a, 21b, ---, which are mounted separated by predetermined spaces from each other on each of four walls to correspond with the height of the up/down movement of the vacuum nozzle 2. Similarly, light sources 22 to 26 are composed of a plurality of LED light sources 22a, 22b, ---; 23a, 23b, ---; 24a, 24b, ---; 25a, 25b; ---; 26a, 26b, ---, respectively, which are mounted separated by predetermined spaces from each other at respectively predetermined heights on each of four walls of the illumination unit 20.

Furthermore, a light source 30 (which corresponds to the second light source 10) for front lighting the absorbed component, like a BGA, is mounted at the bottom level. Light source 30 is (composed of a plurality of LED light sources 30a, 30b, --- which are mounted separated by predetermined spaces on each of four walls of the illumination unit 20. At the top level of the illumination unit 20 is also disposed a light source 40 composed of a plurality of LED light sources 40a, 40b, ---, mounted separated by predetermined spaces on each of four walls. The light source 40 lights a tapered surface 41a formed on the lower portion of a ceiling 41 placed at the top of the illumination unit 20. The light reflected off the tapered surface 41a is directed downward as an auxiliary light source for back lighting the component absorbed by vacuum nozzle 2.

Figure 9:
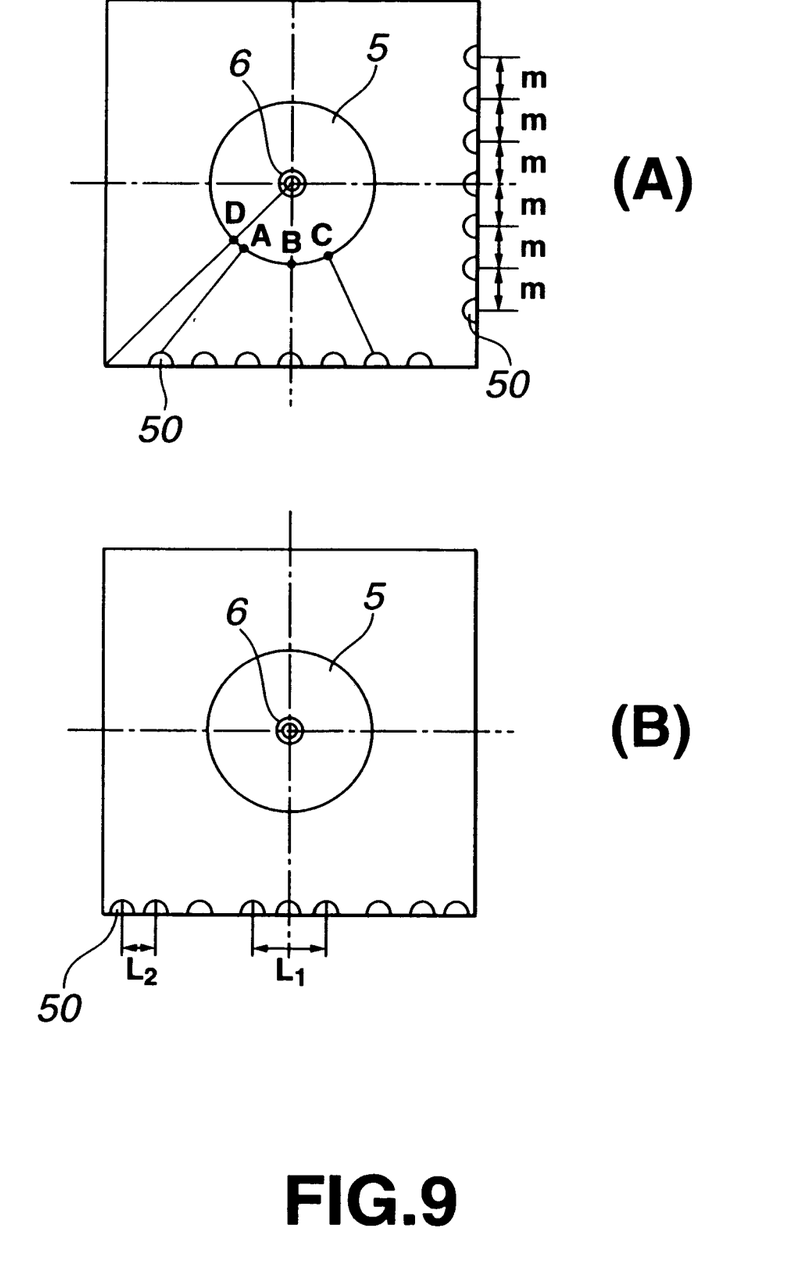
FIG. 9 depicts the difference of illumination of the tapered surface depending on the different dispositions of light sources.

Since the tapered surface 5 is conical and the cross section of the illumination unit is substantially rectangular, the distance between each of the LED light sources and the tapered surface is not equal and the tapered surface is not lighted evenly if the LED light sources are mounted separated by equal spaces on the walls. In other words, if LED light sources 50 are placed with equal spaces m between them as shown in FIG. 9(A), the distance between each of the LED light sources and the tapered surface differs, and consequently the area of point B is lighted brightest, points C and A are gradually lighted Less brightly and the area of point D is lighted most dimly. In order to light the tapered surface evenly, the LED light sources located closer to the tapered surface are preferably mounted separated by a wider space L1 and the ones located further from the tapered surface are mounted separated by a narrower space L2 as shown in FIG. 9(C3).

Figure 10:
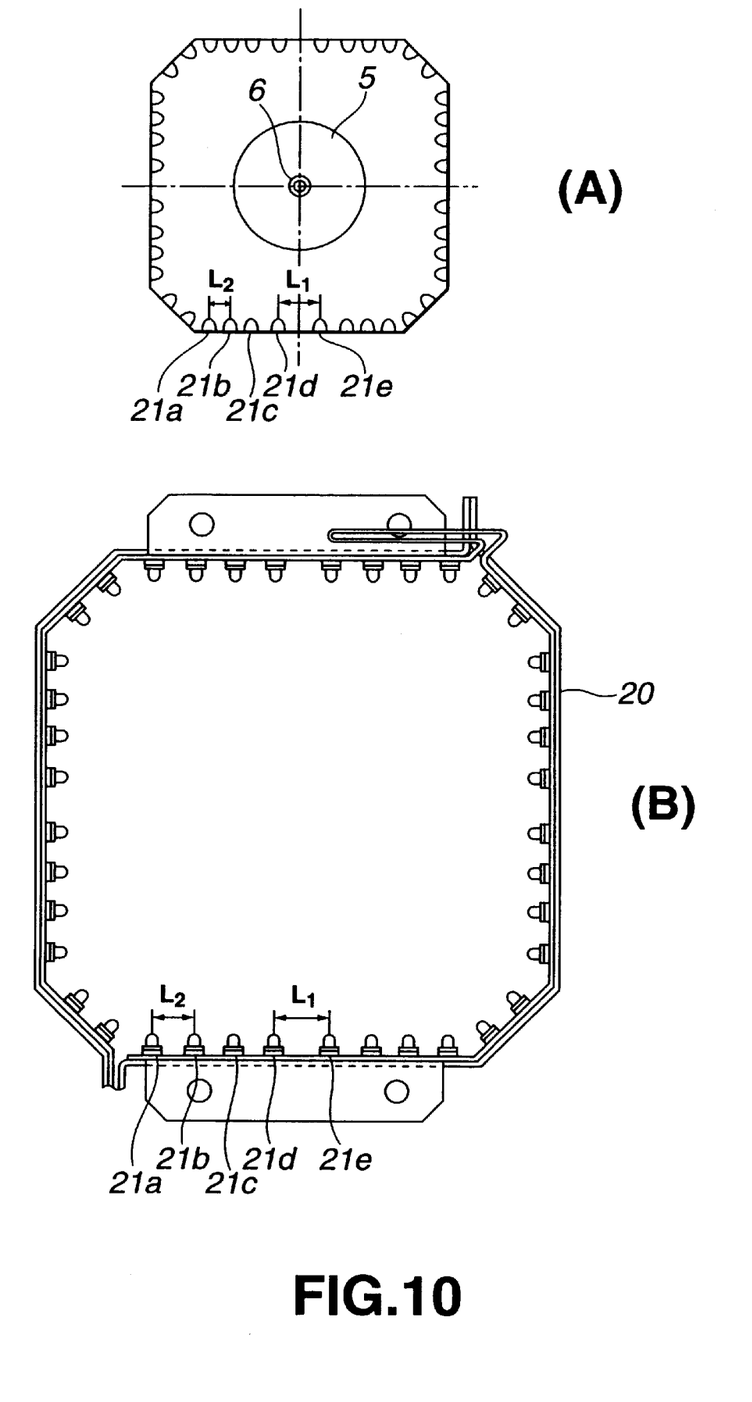
FIG. 10 snows the disposition of light sources separated by different sized spaces. (A) shows a schematic disposition of light sources and (B) shows the actual cross section view.

Thus, each LED of the light sources 21 to 26, 30 and 40 in FIG. 8 is mounted separated by different sized spaces as mentioned above. As examples, FIG. 10(A) shows a schematic disposition of the light source 21, and FIG. 10(B) shows its actual cross sectional view. At each LED light source positioned in the lower portion of the illumination unit 20 shown in FIG. 10, the space L1 between the LED 21d and 21e (located closer to the tapered surface 5) is larger than the space L2 between the LED 21a and 21b which are located further from the tapered surface. The spaces between the LEDs become narrower toward the corners of the rectangular walls. Since the LED arrangement mentioned above is applied to each of four walls, the tapered surface is lighted with an even brightness by each LED light source, and can attain back lighting with even brightness.

The actual spaces between LEDs will be determined by calculations or actual measurements of brightness on the tapered surface so that the tapered surface is lighted with even brightness.

Figure 11:
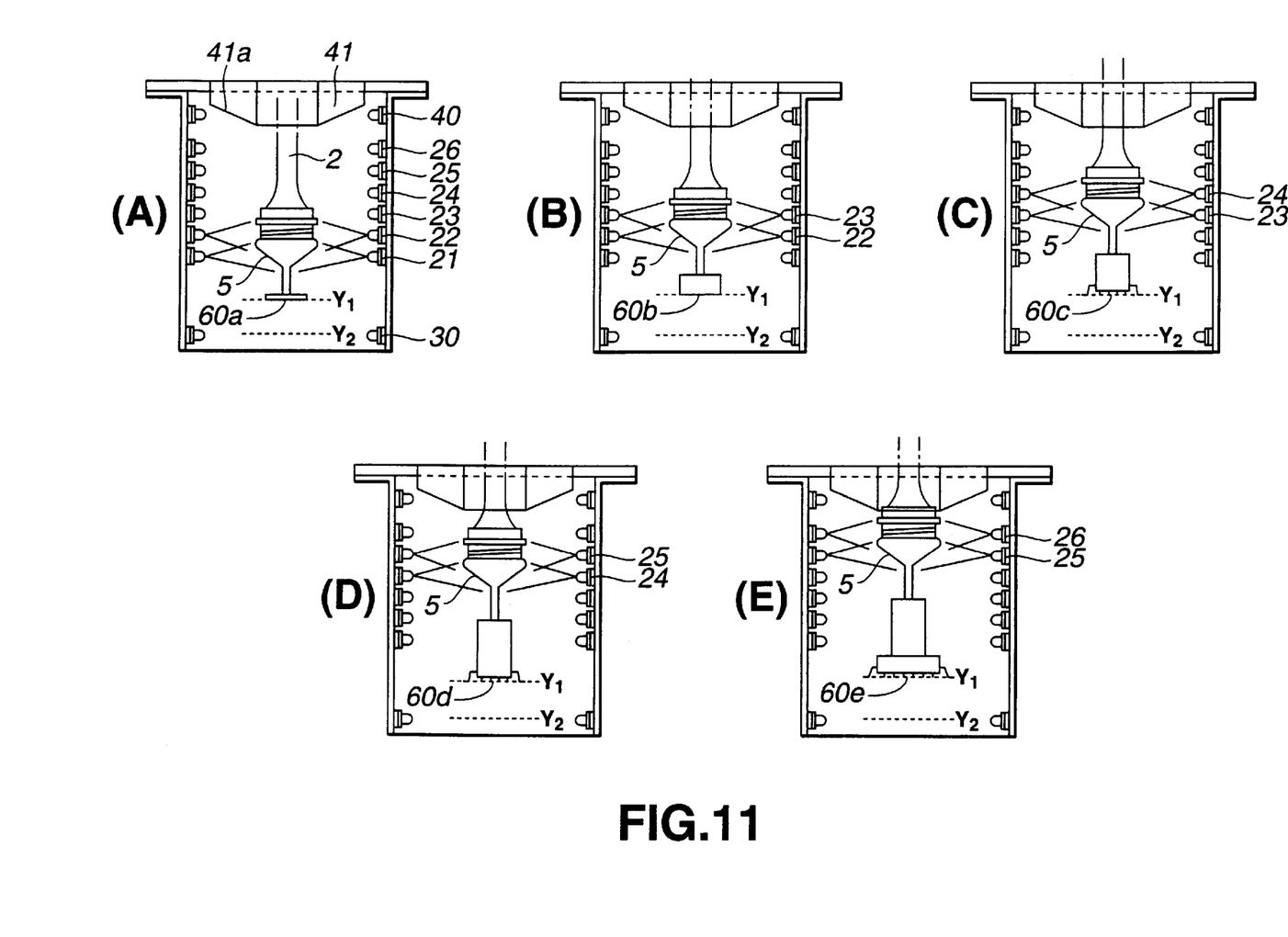
FIG. 11 is a series of diagrams illustrating the selective turning on and off of light sources in response to the thickness of the absorbed component.

FIG. 11 is a series of diagrams illustrating light sources 21 to 26 for back lighting being selectively turned on and off in accordance with the up/down movement of the vacuum nozzle 2, where Y1 indicates the height of the component to be recognized and YZ indicates the height of the recognizing camera. When the absorbed component 60a is very thin or no component is absorbed, the light sources 21 and 22 at the lower level and second lowest level are turned on as shown in FIG. 11(A). As in FIG. 11(B) to (E), the light sources 22, 23; 23, 24; 24, 25; 25, 26 located near the tapered surface 5 are selectively turned on as the vacuum nozzle moves upward from the height Y1 in response to the thickness of the absorbed component. This means can avoid excessive light intensity on an unnecessary portion of the tapered surface 5, prevent bad effects in recognition of the component, and results in a reduction of power consumption.

As explained above, according to the present invention, the tapered surface is formed adjacent the suction surface of the nozzle as a light diffusing surface. The angle of the tapered surface with respect to the nozzle axis is set in such a manner that the light from the first light source is reflected/diffused thereon on the upside of the component and the light from the second light source is reflected/diffused to the side of the nozzle. Therefore, optimum lighting using back lighting or front lighting can be chosen according to the type of the component without additional diffusion plates, resulting in precise recognition of the component.

We claim:

1. An apparatus for recognizing an absorbed component comprising:

means for absorbing the component having a center axis and a tapered, light-diffusing surface adjacent the point of absorption which is larger than the absorbed component;

means for lighting the component comprising a first light source for lighting the component from above and a second light source for lighting the component from below; and means for recognizing the component including means for detecting the contour of the tapered surface;

wherein the optical axis of the first light source is set to an angle $\alpha$ with the center axis, the angle of the tapered surface with the center axis is set to $\beta$, the optical axis of the second light source is set to an angle $\gamma$ with the center axis, and the relation among the aforementioned angles $\alpha$, $\beta$, $\gamma$ is set to:

$(\pi/2+\beta)>\alpha$ and $(\pi/2-\beta)>\gamma$.

2. The apparatus of claim 1, wherein only the image of the component adjacent to the detected contour of said tapered surface is processed.

3. The apparatus as set forth in claim 1, wherein the point of absorption is covered with light absorbing material.

4. An apparatus for recognizing an absorbed component comprising:

a vacuum nozzle including a main body portion with a tapered surface formed at the suction surface side of said nozzle as a light diffusing surface;

a first light source and a second light source for lighting said component, wherein said tapered surface is formed in such a manner that said component is lighted by back lighting from said first light source via said tapered surface and is lighted by front lighting from said second light source; and a recognizing camera disposed to capture the image of said component;

wherein a plurality of first light sources are mounted separated by different spaces to surround the vacuum nozzle so that the tapered surface is lighted with even brightness;

wherein said first light sources are mounted at multiple heights in the direction of the up/down movement of said vacuum nozzle; and wherein predetermined first light sources facing said tapered surface of said vacuum nozzle are selectively turned on according to the up/down movement of said vacuum nozzle.

5. The apparatus of claim 4 wherein the main body portion has a larger outer size than that of said component.

* * * * *